United States Patent
Maurer et al.

(10) Patent No.: US 8,112,290 B2
(45) Date of Patent: Feb. 7, 2012

(54) METHODS FOR DELIVERING A DRUG TO A HOSPITAL PATIENT FOR SHORT-TERM USE WHILE MINIMIZING LONG-TERM USE OF THE DRUG

(75) Inventors: George Raymond Maurer, Dunellen, NJ (US); Robert Barnett Jones, Summit, NJ (US)

(73) Assignee: Adolor Corporation, Exton, PA (US)

( * ) Notice: Subject to any disclaimer, the term of this patent is extended or adjusted under 35 U.S.C. 154(b) by 442 days.

(21) Appl. No.: 12/467,016

(22) Filed: May 15, 2009

(65) Prior Publication Data

US 2009/0287501 A1 Nov. 19, 2009

Related U.S. Application Data

(60) Provisional application No. 61/054,016, filed on May 16, 2008.

(51) Int. Cl.
*G06Q 50/00* (2006.01)
(52) U.S. Cl. .......................................... 705/2
(58) Field of Classification Search ........................ 705/2
See application file for complete search history.

(56) References Cited

U.S. PATENT DOCUMENTS

| | | | |
|---|---|---|---|
| 5,692,502 A | 12/1997 | Alpert | |
| 5,803,906 A | 9/1998 | Pratt et al. | |
| 5,833,599 A | 11/1998 | Schrier et al. | |
| 6,045,501 A | 4/2000 | Elsayed et al. | |
| 6,066,091 A | 5/2000 | Riviere et al. | |
| 6,267,116 B1 | 7/2001 | McMichael | |
| 6,270,455 B1 | 8/2001 | Brown | |
| 6,315,720 B1 | 11/2001 | Williams et al. | |
| 6,471,645 B1 | 10/2002 | Warkentin et al. | |
| 6,547,726 B2 | 4/2003 | Pratt et al. | |
| 6,561,977 B2 | 5/2003 | Williams et al. |
| 6,575,169 B2 | 6/2003 | McMichael |
| 6,581,606 B2 | 6/2003 | Kutzko et al. |
| 6,592,517 B2 | 7/2003 | Pratt et al. |
| 6,658,396 B1 | 12/2003 | Tang et al. |
| 6,755,784 B2 | 6/2004 | Williams et al. |
| 6,824,512 B2 | 11/2004 | Warkentin et al. |
| 6,869,399 B2 | 3/2005 | Williams et al. |
| 6,942,614 B1 | 9/2005 | Kutzko et al. |
| 6,949,081 B1 | 9/2005 | Chance |
| 7,081,095 B2 | 7/2006 | Lynn et al. |
| 7,141,018 B2 | 11/2006 | Williams et al. |
| 7,155,396 B2 | 12/2006 | Yuyama et al. |
| 2001/0016681 A1 | 8/2001 | Pratt et al. |
| 2001/0039373 A1 | 11/2001 | Cunningham et al. |
| 2002/0111542 A1 | 8/2002 | Warkentin et al. |
| 2002/0115915 A1 | 8/2002 | Pratt et al. |
| 2002/0161607 A1 | 10/2002 | Subich |
| 2003/0097220 A1 | 5/2003 | Agur et al. |
| 2003/0144877 A1 | 7/2003 | Goldmann et al. |
| 2004/0193446 A1 | 9/2004 | Mayer et al. |
| 2005/0049464 A1 | 3/2005 | Lassers et al. |
| 2005/0124863 A1 | 6/2005 | Cook |
| 2006/0173714 A1 | 8/2006 | Grotzinger, Jr. |
| 2006/0281978 A1 | 12/2006 | Crucilla |
| 2007/0065363 A1 | 3/2007 | Dalal et al. |
| 2007/0179809 A1 | 8/2007 | Brown et al. |
| 2007/0213598 A1 | 9/2007 | Howard et al. |
| 2007/0255595 A1 | 11/2007 | Nickell |
| 2007/0260487 A1 | 11/2007 | Bartfeld et al. |
| 2008/0065418 A1 | 3/2008 | Byrom et al. |

*Primary Examiner* — Gerald J. O'Connor
*Assistant Examiner* — John Pauls
(74) *Attorney, Agent, or Firm* — Feldman Gael, P.A.; Walter C. Frank

(57) ABSTRACT

Novel methods for delivering a drug to hospital patients for short-term in-hospital use while minimizing long-term use of the drug. Embodiments are provided in which hospitals are identified which may be eligible to treat patients, for example, perform certain types of surgery, and which have measures in place to limit use of the drug to short-term use. The identified hospitals are preferably registered in a storage medium, including computer readable storage media, and may be authorized to receive the shipments of the drug. The received drug may then be dispensed to the patient.

54 Claims, No Drawings

METHODS FOR DELIVERING A DRUG TO A HOSPITAL PATIENT FOR SHORT-TERM USE WHILE MINIMIZING LONG-TERM USE OF THE DRUG

CROSS REFERENCE TO RELATED APPLICATIONS

This application claims the benefit of U.S. Provisional Application Ser. No. 61/054,016, filed May 16, 2008, the disclosure of which is hereby incorporated herein by reference in its entirety.

FIELD OF THE INVENTION

The present invention relates to novel methods for delivering drugs to hospital patients. More particularly, the present invention relates to novel methods for delivering drugs to hospital patients for short-term use while minimizing long-term use of the drugs.

BACKGROUND OF THE INVENTION

In the course of an examination of a patient by a health care practitioner, including patients suffering from one or more diseases and/or disorders such as, for example, one or more disorders or dysfunctions of the gastrointestinal system, the health care practitioner may determine that the patient's condition may be improved by the administration of a drug, such as a drug that may prevent and/or alleviate disorders or dysfunctions of the gastrointestinal system. In connection with the health care practitioner's diagnosis of the patient, and the identification of one or more courses of treatment that may address the patient's condition, including the administration of one or more drugs, it may also be necessary to consider the potential for the course of treatment to produce undesired observed effects in the patient. For example, a drug may have desirable curative or ameliorative properties for a particular disease or disorder, and thus may be advantageously prescribed to the patient to address the patient's medical needs. However, in addition to the drug's curative or ameliorative properties, the possible observation of one or more adverse events may also be associated with the drug. These observed adverse events may occur, for example, when the drug is administered at higher doses, and/or when the drug is administered for longer periods of time. Generally speaking, there is a continuous balance that a health care practitioner seeks to achieve between administering a drug in a sufficient dosage, at sufficient frequencies, and for a sufficient length of time to obtain the desired beneficial effects, while at the same time avoiding the administration of the drug in excessive dosages, too frequently, or for too long a period of time which may result in the observation of one or more undesired adverse events.

For certain drugs, curative or ameliorative properties may be realized when they are administered to patients for shorter periods of time, while a risk of adverse events may be observed when the drug is administered for longer periods of time. Health care practitioners may be therefore faced with the difficult task of ensuring that a particular drug is administered to a patient in a hospital environment, or administered for a desired period of time as in the case, for example of short-term use, while minimizing or avoiding the administration of the drug in an undesired environment, such as outside of the hospital, or for undesired periods of time as in the case, for example, of long-term use.

To avoid the use of drugs in a manner that may elicit the undesired observation of adverse events, it is generally necessary that the health care practitioners also be educated regarding the potential for such observed adverse events. It may also be necessary to prevent health care practitioners who are not educated regarding a drug's potential to cause observed adverse events from administering the drug to patients, or from gaining access to the drug.

Accordingly, there is a need in the medical community for improved methods that provide the necessary checks and controls to ensure that drugs are administered to patients for the appropriate period of time, in the appropriate environment, and at the proper frequency and dosages. The present invention is directed to these, as well as other important ends.

SUMMARY OF THE INVENTION

The present invention is directed to methods for the delivery to patients, particularly hospital patients, of drugs, especially drugs whose use is preferably curtailed or restricted to short-term use in hospitals.

Specifically, in one embodiment of the invention, there are provided methods for delivering drugs to hospital patients for short-term use while minimizing long-term use of the drugs, wherein the methods comprise:

(a) identifying hospitals which may be eligible to dispense the drug;

(b) providing the hospitals with literature regarding use of the drug;

(c) identifying a subpopulation of the hospitals which treat the patients and which have measures in place to limit use of the drug to short-term use;

(d) registering the subpopulation in a storage medium;

(e) authorizing the subpopulation to receive shipment of the drug; and (f) dispensing the drug to the patients in the subpopulation for short-term use.

The methods described herein provide novel and effective means for delivering, controlling and authorizing the distribution and administration of drugs to patients that may benefit from the use of the drug. The methods of the present invention include a variety of checks and controls which ensure that the drug is used in hospitals for short-term periods, and which minimize long-term use of the drug. Distribution of the drug to hospitals that may not be eligible to receive the drug may be advantageously prevented with the present methods. Distribution of the drug to patients who are not hospital patients may also be advantageously prevented. In the case of drugs whose long-term use is associated with the observation of adverse events, the present methods may be particularly beneficial and advantageous, as they may be useful in minimizing and even in certain circumstances avoiding the occurrence of such observed adverse events.

These and other aspects of the invention will become more apparent from the following detailed description.

DETAILED DESCRIPTION OF THE INVENTION

The present invention is generally directed to methods for the delivery of drugs to patients, particularly hospital patients, for short-term use, while minimizing long term use of the drug. The term "drug", as used herein, refers to any substance which is intended for use in the diagnosis, cure, mitigation, treatment or prevention of disease, or to affect the structure or function of the body. The term "patient", as used herein, refers to animals, including mammals, preferably humans. The methods of the present invention offer a variety of checks and balances that may be employed to tightly regulate and control the delivery of drugs to hospitals and the administration of drugs to hospital patients. The present methods may be advantageously used to deliver and administer drugs to patients within the confines of the hospital, and thereby minimize or avoid the unauthorized use or administration of the drug as may be the case, for example, outside the tightly controlled and monitored environment of a hospital. Thus, the methods described herein are particularly useful for delivering drugs to hospital inpatients or hospitalized patients. The term "hospital inpatient", as used herein, refers to a hospitalized patient, i.e., a patient whose care or treatment is performed in a hospital. In preferred embodiments, the care or treatment of a hospital inpatient may require a patient's stay in the hospital of at least about one day. In certain embodiments, the patient may be required to stay in the hospital for a period of from about 1 day to about 10 days (and all combinations and subcombinations of ranges of days and specific numbers of days therein). More preferably, the patient may be required to stay in the hospital for a period of from about 2 or 3 days to about 7 days.

The present methods advantageously enable a hospital to deliver drugs to hospital patients while minimizing long-term use of the drug. The term "minimize", as used in reference to the long-term use of a drug, generally means that there is an avoidance rate of using the drug long-term of greater than about 50%. Preferably, the avoidance rate is greater than about 55%, with an avoidance rate of greater than about 60% being more preferred. Even more preferably, the avoidance rate is greater than about 65%, with an avoidance rate of greater than about 70% being still more preferred. Yet more preferably, the avoidance rate is greater than about 75%, with an avoidance rate of greater than about 80% being still more preferred. In even more preferred embodiments, the avoidance rate is greater than about 85%, with an avoidance rate of greater than about 90% being yet more preferred. Still more preferably, the avoidance rate is greater than about 95%. In particularly preferred embodiments, a drug may be delivered to hospital patients with substantially no long-term use (i.e., nearly or up to a 100% avoidance rate).

The methods of the present invention may be particularly useful for the delivery of drugs whose long-term use may be associated with the observation of one or more adverse events. Thus, the methods of the present invention may be used to minimize the occurrence of observed adverse events. The term "minimize", as used in reference to the observation of adverse events that may be associated with the long-term use of a drug, generally means that there is an avoidance rate in observing adverse events of greater than about 50%. Preferably, the avoidance rate is greater than about 55%, with an avoidance rate of greater than about 60% being more preferred. Even more preferably, the avoidance rate is greater than about 65%, with an avoidance rate of greater than about 70% being still more preferred. Yet more preferably, the avoidance rate is greater than about 75%, with an avoidance rate of greater than about 80% being still more preferred. In even more preferred embodiments, the avoidance rate is greater than about 85%, with an avoidance rate of greater than about 90% being yet more preferred. Still more preferably, the avoidance rate is greater than about 95%. In particularly preferred embodiments, a drug may be delivered to hospital patients with substantially no observation of adverse events (i.e., nearly or up to a 100% avoidance rate).

The drug delivery methods of the present invention preferably involve, inter alia, the identification of hospitals that may be eligible to dispense the drug. In certain preferred aspects of the present invention, the term "dispense" may refer to filling prescriptions or physician orders by pharmacies, particularly hospital pharmacies, and the distribution of the drug by the pharmacies to healthcare practitioners within the hospital for administration to the patient. Exemplary healthcare practitioners include, for example, surgeons, nurses, anesthesiologists, certified nurse anesthetists, pharmacists and the like. In certain other preferred aspects of the invention, the term "dispense" may refer to the administration of the drug by a healthcare practitioner to the patient which includes, for example, oral or parenteral administration depending, for example, on the particular form of the involved drug.

In preferred embodiments of the invention, hospitals that may be eligible to dispense the drug include, for example, hospitals that may be competent to perform certain types of surgery and/or hospitals that are acute care hospitals. The term "surgery", as used herein, refers to any methodical action of the hand, or of the hand with instruments, on a patient, to produce a curative or remedial effect, and includes, for example, abdominal surgery. The term "abdominal surgery", as used herein, broadly refers to surgical procedures that involve opening the abdomen such as, for example, laparotomies, including bowel resection surgery, Caesarian births, and sterilization procedures. The term "acute care hospital", as used herein, refers to hospitals that are capable of treating patients for a brief but severe episode of illness, disease or disorder. Acute care hospitals typically seek to discharge the patient as soon as the patient is deemed healthy and stable, often with appropriate discharge instructions. In preferred embodiments of the invention, hospital patients for whom the present drug delivery methods may be employed are acute care patients including, for example, surgery patients, with abdominal surgery patients being preferred. Accordingly, eligible hospitals are preferably those which have health care practitioners that are competent to perform abdominal surgery. In preferred embodiments, the hospitals involved in the methods described herein are competent to perform bowel resection surgery, especially bowel resection surgery in which the two remaining ends of the bowel are sewn, stapled, or both sewn and stapled together (i.e., bowel resection surgery involving intestinal anastomosis).

The methods of the present invention may be employed to deliver a wide variety of drugs to patients, depending on the involved illness, disease, or disorder. Drugs delivered to patients using the methods described herein are preferably drugs that are only used for limited periods of time (i.e., drugs that are used short-term), and whose extended use (i.e., long-term use) is preferably avoided. Accordingly, the methods of the present invention are particularly advantageous for delivering drugs to patients whose illness, disease or disorder is typically of short duration, and who would therefore be prescribed one or more drugs to treat the illness, disease or disorder for a short period of time, but whose disease or disorder may recur or continue beyond the short period of time.

In preferred embodiments, the term "short-term use", as used herein, may refer to the administration to a patient of no more than about 20 doses of the drug. Accordingly, the term "long-term use", as used herein, may refer to the administration to a patient of more than about 20 doses of the drug. The term "dose", as used herein, refers to physically discrete units suited as unitary dosages for ingestion by the particular patient to be treated. Each unit may contain a predetermined quantity of one or more active ingredients, calculated to produce the desired therapeutic effect, in association with a suitable pharmaceutical carrier. In preferred embodiments, the patient may receive no more than about 17 doses of the drug, with no more than about 15 doses of the drug being even more preferred. More preferably, the patient may receive no more than about 12 doses of the drug, with no more than about 10 doses of the drug being even more preferred. Still more preferably, the patient may receive no more than about 8 doses of the drug, with no more than about 6 doses of the drug being yet more preferred. In certain preferred embodiments, the patient may receive no more than about 4 doses of the drug including, for example, no more than about 3 doses, no more than about 2 doses or no more than about 1 dose of the drug.

In alternate preferred embodiments, the patient may be administered a total of from about 10 to about 20 doses of the drug (and all combinations and subcombinations of ranges of doses and specific numbers of doses therein). More preferably, the patient may receive a total of from about 14 to about 16 doses of the drug, with a total of about 15 doses being even more preferred.

In still other preferred embodiments, the patient may be administered a total of from about 1 to about 12 doses of the drug (and all combinations and subcombinations of ranges of doses and specific numbers of doses therein). More preferably, the patient may receive a total of from about 2 to about 10 doses of the drug, with a total of from about 4 to about 8 doses being even more preferred. Still more preferably, the patient may receive a total of about 6 or about 7 doses of the drug.

In embodiments of the present invention in which the patient is a surgery patient, for example, an abdominal surgery patient, the patient may advantageously be administered the drug prior to surgery, after surgery, or both prior to and after surgery. Accordingly, in the context of the present methods, the drug may preferably be delivered to the patient prior to surgery, after surgery, or both prior to and after surgery. In embodiments involving surgery patients, the term "short-term use" may refer to the administration to a patient of the drug for no more than about 10 days after surgery. Accordingly, the term "long-term use", as used herein in reference to surgery patients, may refer to the administration to a patient of the drug for more than about 10 days after surgery. Preferably, the patient may be administered the drug for no more than about 8 days after surgery, with the patient being administered the drug for no more than about 7 days after surgery being more preferred. Even more preferably, the patient may be administered the drug for no more than about 6 days after surgery, with the patient being administered the drug for no more than about 5 days after surgery being still more preferred. Yet more preferably, the patient may be administered the drug for no more than about 4 days after surgery, with the patient being administered the drug for no more than about 3 days after surgery being even more preferred. In certain particularly preferred embodiments, the patient may be administered the drug for no more than about 2 days after surgery or no more than about 1 day after surgery.

In alternate preferred embodiments, the drug may be administered to the patient for about 5 to about 10 days after surgery (and all combinations and subcombinations of ranges of days and specific numbers of days therein). More preferably, the patient may be administered the drug for about 6 to about 8 days after surgery, with the patient being administered the drug for about 7 days after surgery being even more preferred.

In still other preferred embodiments, the drug may be administered to the patient for about 1 to about 5 days after surgery (and all combinations and subcombinations of ranges of days and specific numbers of days therein). More preferably, the patient may be administered the drug for more than about 1 day to about 4 days after surgery, with the patient being administered the drug for about 2 days or about 3 days after surgery being even more preferred.

In embodiments of the invention, including embodiments involving surgery patients, such as abdominal surgery patients, the drug may preferably be administered to the patient from about once a day after surgery to about three times a day after surgery. More preferably, the drug may be administered to the patient about twice a day after surgery. Also in embodiments involving surgery patients, including abdominal surgery patients, a total of from about 10 to about 20 doses of the drug may preferably be administered to the patient after surgery (and all combinations and subcombinations of ranges of doses and specific doses therein). More preferably, the patient may be administered a total of from about 12 to about 15 doses of the drug after surgery, with a total of about 14 doses of the drug being administered after surgery being even more preferred.

In alternate embodiments of the invention, including embodiments involving surgery patients, such as abdominal surgery patients, a total of from about 1 to about 12 doses of the drug may preferably be administered to the patient after surgery (and all combinations and subcombinations of ranges of doses and specific doses therein). More preferably, the patient may be administered a total of from about 3 to about 10 doses of the drug after surgery, with a total of about 5 to about 8 doses of the drug being administered after surgery being even more preferred. Still more preferably, the patient may be administered about 6 or about 7 doses of the drug after surgery.

In embodiments involving surgery patients, including abdominal surgery patients, the term "short-term use" may refer to the administration of the drug to the patient for less than about 1 day to about 5 days prior to surgery (and all combinations and subcombinations of ranges of days and specific numbers of days therein). Accordingly, in embodiments involving surgery patients, the term "long-term use" may refer to the administration to a patient of the drug for more than about 5 days before surgery. Preferably, the patient may be administered the drug for less than about 1 day to about 2 days prior to surgery, with the patient being administered the drug for less than about 1 day to about 1 day prior to surgery being more preferred.

The term "less than about 1 day" may refer to the administration of the drug to the patient from about 1 minute to less than about 24 hours prior to surgery (and all combinations and subcombinations of ranges of time and specific values of time therein). Preferably, the patient may be administered the drug from about 15 minutes to about 12 hours prior to surgery, with from about 30 minutes to about 5 hours being more preferred.

In alternate preferred embodiments, the term "short-term use" may refer to the administration of about 0 to about 5 doses of the drug prior to surgery (and all combinations and subcombinations of ranges of doses and specific doses therein). Accordingly, in embodiments involving surgery patients, the term "long-term use" may refer to the administration to a patient of more than about 5 doses of the drug prior to surgery. More preferably, the patient may be administered about 1 to about 3 doses of the drug prior to surgery, with about 1 dose of the drug being administered prior to surgery being even more preferred.

In accordance with embodiments of the present invention, the methods described herein may be particularly useful for delivering drugs to patients suffering from gastrointestinal dysfunction. The term "gastrointestinal dysfunction", as used herein, refers to a variety of disorders of the gastrointestinal system including, for example, disorders of the gastrointestinal system that may be associated with opioids, including exogenous and/or endogenous opioids, gastrointestinal disorders due to abdominal injury and/or surgery, childbirth, and sterilization procedures, and the like. The present methods are also useful for delivering drugs to patients who may be expected to develop gastrointestinal dysfunction. For example, patients who require abdominal surgery such as, for example, bowel resection surgery, may be expected to develop gastrointestinal dysfunction. Thus, the methods described herein may be advantageously used in the prevention, inhibition and/or treatment of gastrointestinal dysfunction. Examples of gastrointestinal dysfunction that may be prevented, inhibited and/or treated with the methods of the present invention include, for example, opioid-induced constipation (OIC), opioid-induced bowel dysfunction (OBD), ileus, including postpartum ileus and postsurgical ileus, idiopathic constipation, irritable bowel syndrome, and various combinations of two or more of these disorders. In preferred embodiments, the present methods may be used for preventing, inhibiting and/or treating ileus.

Mu opioid antagonist compounds, and particularly peripherally-acting mu opioid antagonist compounds that do not substantially cross the blood-brain barrier into the CNS including, for example, alvimopan and N-methylnaltrexone, are known in the literature as being useful in relation to their activity on the gastrointestinal tract. Alvimopan is particularly useful in the prevention, inhibition and/or treatment of ileus resulting from abdominal surgery and, accordingly, is a preferred drug for use in embodiments of the present invention. Alvimopan may be provided, for example, in the form of a hot-melt gelatin capsule, which preferably comprises alvimopan suspended in water-soluble polyethylene glycol. N-Methylnaltrexone may be useful in connection with embodiments of the present invention that involve the prevention, inhibition and/or treatment of opioid-induced constipation (OIC) and/or opioid-induced bowel dysfunction (OBD).

The dosage of the drug that will be most suitable for use in the present methods will depend on a variety of factors including, for example, the particular illness, disease or disorder which is being prevented, inhibited or treated, the particular active ingredient of the chosen drug, and the physiological characteristics of the particular patient. In certain embodiments involving mu opioid antagonist compounds, especially peripherally-acting mu opioid antagonist compounds, for example, alvimopan or N-methylnaltrexone, the quantity of active ingredient in each dose that is delivered to a patient may vary depending upon various factors such as, for example, the pharmacodynamic characteristics of the particular agent and its mode and route of administration, the age, health and weight of the recipient, the nature and extent of the symptoms, the kind of concurrent treatment, the frequency of treatment, and the effect desired. For example, in certain embodiments, the drug may be formulated for oral administration, while in other embodiments, the drug may be formulated for parenteral administration which includes, for example, administration intravenously, intramuscularly, subcutaneously, intraocularly, intrasynovially, transepithelially including transdermally, ophthalmically, sublingually and buccally. A preferred form of parenteral administration is intravenous administration. Generally speaking, oral administration may require higher dosages.

In certain preferred embodiments, including embodiments involving peripheral mu opioid antagonist compounds, such as alvimopan, each dose may be formulated for oral administration as described, for example, in U.S. Pat. No. 5,434,171, the disclosure of which is hereby incorporated herein by reference, in its entirety. In accordance with such embodiments, each dose delivered to the patient preferably contains from about 5 to about 20 mg of active ingredient (and all combinations and subcombinations of ranges of amounts of active ingredient and specific amounts therein). More preferably, the peripheral mu opioid antagonist compound is administered in a dose of from about 10 to about 15 mg, with a dose about 12 mg being even more preferred.

In other preferred embodiments, including embodiments involving peripheral mu opioid antagonist compounds, such as alvimopan, each dose may be formulated for parenteral administration, particularly intravenous administration as described, for example, in copending U.S. application Ser. No. 11/143,535, filed Jun. 2, 2005, the disclosure of which is hereby incorporated herein by reference, in its entirety. In accordance with such embodiments, each dose delivered to the patient preferably contains from about 0.1 to about 6 mg of active ingredient (and all combinations and subcombinations of ranges of amounts of active ingredient and specific amounts therein). More preferably, the peripheral mu opioid antagonist compound is administered in a dose of from about 0.5 to about 5 mg, with a dose of from about 1 mg to about 3 mg being even more preferred.

In accordance with embodiments of the present invention, hospitals may be provided with educational materials to ensure proper use, including prescribing and dispensing of the drug. A wide variety of educational materials may be employed to ensure proper prescribing and dispensing according to the methods described herein, including, for example, various forms of literature materials. The term "literature", as used herein, refers to a variety of materials including, for example, product information, educational brochures, continuing education monographs, videotapes and the like, and various combinations of two or more of such materials. Depending on the nature and the type of the involved materials, the literature may be paper-based or may be in electronic format. In preferred embodiments, the literature may describe benefits and/or risks associated with the drug, and may further include instructions for properly dispensing and administering the drug. For example, with regard to benefits, the literature may describe, for example, advantageous medical benefits that may be realized by using the particular drug, including the beneficial ameliorative or curative properties associated with ingesting the drug in connection with the treatment, prevention or inhibition of a particular illness, disease and/or disorder. In addition to or instead of describing such benefits, the literature materials may describe possible disadvantageous aspects associated with the drug including, for example, undesirable observed adverse events, and the like, that may be associated with the drug or when the drug is used in certain ways such as, for example, when the drug is used long-term. The term "observed adverse event", as used herein, refers to an observed consequence other than the one(s) for which a drug is used, especially on a tissue or organ system other than the one sought to be benefited by its administration. Examples of adverse events within the context of the present invention include, for example, ischemic cardiovascular events, such as myocardial infarctions.

Accordingly, in embodiments involving patients suffering from or who are expected to suffer from gastrointestinal dysfunction, the literature may describe the preventive, ameliorative and/or curative properties of a drug, for example, a peripheral mu opioid antagonist compound, that may be prescribed for the prevention, inhibition and/or treatment of gastrointestinal dysfunction. In addition to, or instead of describing the beneficial properties of the drug, the literature may describe possible disadvantageous properties, for example, the occurrence of one or more adverse events that may have been observed with long-term use of the drug.

In preferred embodiments, the literature may take the form of, inter alia, a hospital registration card or form which includes dispensing and administration instructions. In preferred embodiments, the registration card or form may require that the hospital acknowledge that it has complied with aspects of the methods described herein. The registration card or form may also require that the hospital acknowledge that health care practitioners who are affiliated or associated with the hospital, and who are responsible, for example, for ordering, dispensing and/or administering the drug, have complied with aspects of the present methods. For example, the registration card or form may require that the hospital acknowledge that it has received literature materials, including educational materials that describe the benefits and/or risks associated with ingesting the drug. The registration card or form may also require that the hospital acknowledge that health care practitioners affiliated or associated with the hospital have been provided the literature materials, including educational materials that describe the benefits and/or risks of taking the drug.

Also in preferred embodiments, the registration card or form may require that the hospital acknowledge that it has measures in place to limit use of the drug to short-term use. The term "limit" or "limiting", as used herein in reference to using the drug short-term, generally means that there is a compliance rate of using the drug short-term of greater than about 50%. Preferably, the compliance rate is greater than about 55%, with a compliance rate of greater than about 60% being more preferred. Even more preferably, the compliance rate is greater than about 65%, with a compliance rate of greater than about 70% being still more preferred. Yet more preferably, the compliance rate is greater than about 75%, with a compliance rate of greater than about 80% being still more preferred. In even more preferred embodiments, the compliance rate is greater than about 85%, with a compliance rate of greater than about 90% being yet more preferred. Still more preferably, the compliance rate is greater than about 95%. In particularly preferred embodiments, a drug may be delivered or administered to hospital patients for substantially complete short-term use (i.e., nearly or up to a 100% compliance rate).

The measures that a hospital preferably has in place to limit use of the drug to short-term use may take a variety of forms. Preferably, the measures are in the form of systems, order sets, protocols, guidelines or the like. The term "system", as used herein, refers to a comprehensive, integrated information system designed to manage, inter alia, clinical aspects within a hospital, and may encompass paper-based information processing as well as data processing machines, and may be composed of one or more software components with specialty-specific extensions as well as a large variety of subsystems in medical specialties. The term "order set", as used herein, refers to a set of standardized instructions for the management of a particular disease, condition, or procedural intervention, presented as a group of orders to be individually selected and signed by an authorized prescriber. The term "protocol", as used herein, refers to a step-by-step statement of a procedure routinely used in the care of individual patients to assure that the intended effect is reliably achieved. The term "guideline", as used herein, refers to an evidence-based statement of best practice in the prevention, diagnosis, or management of a given symptom, disease, or condition for individual patients under normal circumstances. Other types of measures that may be employed to limit use of the drug to short-term use, and to minimize long-term use of the drug, will be apparent to one of ordinary skill in the art, once armed with the teachings of the present application. Thus, in accordance with the methods of the present invention, measures are preferably put in place that ensure that the delivery and administration of the drug is limited to short-term use, and also ensure that long-term use of the drug is minimized.

With further reference to literature provided to the hospitals, the registration card or form may also preferably require that the hospital acknowledge that the drug will not be dispensed for outpatient use, and may further require that the hospital acknowledge that the drug will not be transferred to hospitals that are not in full compliance with the methods as described herein. The hospital will preferably complete the registration card or form by providing information requested therein. Information which may be requested of the hospital in the registration card or form may include, for example, the hospital's name, the hospital's identification number, the hospital's address, the identity of the person that has been authorized to fill out the form on the hospital's behalf, and the like. The registration card or form will preferably be returned to an authorized recipient of the registration materials such as, for example, the manufacturer or distributor of the drug, by an appropriate means of transmission, for example, by mail, facsimile transmission or on-line transmission.

Once the registration card or form is returned, the authorized recipient may identify which hospitals are eligible to treat the patients. For example, in embodiments involving acute care patients, such as abdominal surgery patients, particularly bowel resection surgery patients, the authorized recipient may determine whether the hospital is an acute care hospital, including whether the hospital and the health care practitioners therein perform abdominal surgery, including bowel resection surgery. Accordingly, it may be possible to identify from among the entire population of hospitals that have filled out and returned a registration card or form, a subpopulation of suitable hospitals. The hospitals in the subpopulation are preferably those which treat the patients (e.g., hospitals which perform surgery, such as abdominal surgery, particularly bowel resection surgery) and which have measures in place to limit the use of the drug to short-term use, in-hospital use, or short-term in-hospital use and thus minimize long-term use or out-patient use of the drug. Hospitals which do not fill out and return a registration card or form, or which return a card that is incompletely filled out, are not included in the subpopulation.

In accordance with the methods of the present invention, the subpopulation of hospitals is preferably registered in a storage medium such as, for example, a paper-based storage medium or a computer readable storage medium. Suitable paper-based or computer readable storage media which may be employed for registration of the hospitals will be apparent to one of ordinary skill in the art, once armed with the teachings of the present application. The listing of the subpopulation of hospitals is maintained, for example, by the authorized recipient, or by an entity that has been authorized to maintain the listing on behalf of the authorized recipient. Hospitals that are included in the subpopulation, and that are listed in the storage medium, may refer to the listing to conveniently identify other hospitals within the subpopulation. Similarly, the manufacturer or distributor of the drug or other authorized entity, for example, an entity that is authorized to ship drug product, may also refer to the listing to identify hospitals within the subpopulation.

Once registered in the storage medium, the hospitals in the subpopulation may be authorized to receive shipment of the drug. After receiving shipment of the drug, the drug may be prescribed and dispensed to the patient at the desired doses and administration frequencies, as discussed above. In certain embodiments of the invention, the methods may further involve observing and/or monitoring the patient for the possible occurrence of an observed adverse event while the patient is receiving the drug.

In certain embodiments of the invention, hospitals in the subpopulation may transfer the drug to one or more additional hospitals for delivery to patients within the additional hospitals. Such transfer of the drug may occur provided that the one or more additional hospitals are also registered in the storage medium, i.e., the additional hospitals have satisfied the conditions described above to be included in the subpopulation of hospitals. If this condition is met, then the drug may be transferred to the additional hospitals, and the drug may be dispensed to patients in such additional hospitals for short-term use.

When ranges are used herein, all combinations and subcombinations of ranges and specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for delivering a drug to hospital patients for short-term use while minimizing long-term use of the drug, wherein the drug requires compliance with a risk evaluation and mitigation strategy approved by the Food and Drug Administration (FDA) which is designed to minimize the occurrence of an observed adverse event; and wherein the method comprises:
   identifying hospitals that may be eligible to dispense the drug, said eligibility requiring that said hospitals:
     perform abdominal surgery or are acute care hospitals; and
     treat patients who are inpatients;
   providing said identified hospitals with literature regarding use of the drug including dosing recommendations and contraindications, and which describes the observation of an adverse event associated with long-term use of the drug;
     wherein the drug is a peripherally acting mu-opioid receptor antagonist selected from the group consisting of alvimopan and N-methylnaltrexone;
   receiving registration information from said identified hospitals;
   identifying a subpopulation of said identified hospitals which treat the patients and which have said measures in place to limit use of the drug to short-term use;
     wherein said measures comprise order sets, protocols or guidelines, residing on an integrated information system, including a data processing machine, to limit use of the drug to short-term use;
   registering said subpopulation in a computer readable storage medium;
   authorizing said subpopulation to receive shipment of the drug; and
   dispensing the drug to the patients in said subpopulation for short-term use;
     wherein the patients are hospital inpatients and the delivery is limited to in-hospital administration; and
   monitoring the patients for said observed adverse event.

2. A method according to claim 1 wherein long-term use of the drug is associated with the observation of an adverse event.

3. A method according to claim 2 wherein said observed adverse event is an ischemic cardiovascular event.

4. A method according to claim 3 wherein said ischemic cardiovascular event is a myocardial infarction.

5. A method according to claim 1 wherein the patients are acute care patients.

6. A method according to claim 5 wherein said acute care patients are abdominal surgery patients.

7. A method according to claim 6 wherein said abdominal surgery is bowel resection surgery.

8. A method according to claim 6 wherein the delivery of the drug to said abdominal surgery patients is for the treatment or prevention of gastrointestinal dysfunction.

9. A method according to claim 8 wherein said gastrointestinal dysfunction is ileus.

10. A method according to claim 1 wherein said observed adverse event is an ischemic cardiovascular event.

11. A method according to claim 10 wherein said ischemic cardiovascular event is a myocardial infarction.

12. A method according to claim 1 wherein short-term use comprises the delivery to each of the patients of no more than about 20 doses of the drug.

13. A method according to claim 12 wherein no more than about 15 doses of the drug are delivered to each of the patients.

14. A method according to claim 13 wherein no more than about 10 doses of the drug are delivered to each of the patients.

15. A method according to claim 14 wherein no more than about 7 doses of the drug are delivered to each of the patients.

16. A method according to claim 1 wherein short-term use comprises the delivery to each of the patients of a total of from about 10 to about 20 doses of the drug.

17. A method according to claim 16 wherein a total of from about 14 to about 16 doses of the drug is delivered to each of the patients.

18. A method according to claim 17 wherein a total of about 15 doses of the drug is delivered to each of the patients.

19. A method according to claim 1 wherein short-term use comprises the delivery to each of the patients of a total of from about 4 to about 8 doses of the drug.

20. A method according to claim 19 wherein a total of from about 6 to about 7 doses of the drug is delivered to each of the patients.

21. A method according to claim 6 wherein the drug is delivered to said abdominal surgery patients prior to surgery, after surgery, or both prior to and after surgery.

22. A method according to claim 21 wherein short-term use comprises the delivery of the drug to said abdominal surgery patients for no more than about 10 days after surgery.

23. A method according to claim 22 wherein the drug is delivered to said abdominal surgery patients for no more than about 7 days after surgery.

24. A method according to claim 23 wherein the drug is delivered to said abdominal surgery patients for no more than about 5 days after surgery.

25. A method according to claim 24 wherein the drug is delivered to said abdominal surgery patients for no more than about 3 days after surgery.

26. A method according to claim 21 wherein short-term use comprises the delivery of the drug to said abdominal surgery patients for about 5 to about 10 days after surgery.

27. A method according to claim 26 wherein the drug is delivered to said abdominal surgery patients for about 6 to about 8 days after surgery.

28. A method according to claim 27 wherein the drug is delivered to said abdominal surgery patients for about 7 days after surgery.

29. A method according to claim 21 wherein short-term use comprises the delivery of the drug to said abdominal surgery patients for more than about 1 to about 4 days after surgery.

30. A method according to claim 29 wherein the drug is delivered to said abdominal surgery patients for about 2 to about 3 days after surgery.

31. A method according to claim 21 wherein the drug is delivered to said abdominal surgery patients about twice a day after surgery.

32. A method according to claim 21 wherein short-term use comprises the delivery to each of said abdominal surgery patients of a total of from about 10 to about 20 doses of the drug after surgery.

33. A method according to claim 32 wherein a total of from about 12 to about 15 doses of the drug is delivered to each of said abdominal surgery patients after surgery.

34. A method according to claim 33 wherein a total of about 14 doses of the drug is delivered to each of said abdominal surgery patients after surgery.

35. A method according to claim 21 wherein short-term use comprises the delivery to each of said abdominal surgery patients of a total of from about 5 to about 8 doses of the drug after surgery.

36. A method according to claim 35 wherein a total of from about 6 to about 7 doses of the drug is delivered to each of said abdominal surgery patients after surgery.

37. A method according to claim 21 wherein the drug is delivered to said abdominal surgery patients for less than about 1 day to about 5 days prior to surgery.

38. A method according to claim 37 wherein the drug is delivered to said abdominal surgery patients for less than about 1 day to about 2 days prior to surgery.

39. A method according to claim 38 wherein the drug is delivered to said abdominal surgery patients for less than about 1 day to about 1 day prior to surgery.

40. A method according to claim 21 wherein about 0 to about 5 doses of the drug are delivered to each of said abdominal surgery patients prior to surgery.

41. A method according to claim 40 wherein about 1 to about 3 doses of the drug are delivered to each of said abdominal surgery patients prior to surgery.

42. A method according to claim 41 wherein about 1 dose of the drug is delivered to each of said abdominal surgery patients prior to surgery.

43. A method according to claim 1 wherein the drug is alvimopan.

44. A method according to claim 43 wherein said alvimopan is formulated for oral administration.

45. A method according to claim 44 wherein said alvimopan is in the form of a hot-melt gelatin capsule.

46. A method according to claim 45 wherein said hot-melt gelatin capsule comprises alvimopan suspended in water-soluble polyethylene glycol.

47. A method according to claim 44 wherein each dose delivered to each of the patients contains from about 5 to about 20 mg alvimopan.

48. A method according to claim 47 wherein each of said doses contains from about 10 to about 15 mg alvimopan.

49. A method according to claim 48 wherein each of said doses contains about 12 mg alvimopan.

50. A method according to claim 43 wherein said alvimopan is formulated for intravenous administration.

51. A method according to claim 50 wherein each dose delivered to each of the patients contains from about 0.5 to about 5 mg alvimopan.

52. A method according to claim 51 wherein each of said doses contains from about 1 to about 3 mg alvimopan.

53. A method according to claim 1 further comprising the step of:
   (g') transferring said drug from a hospital in said subpopulation to one or more additional hospitals for delivery to a patient within said one or more additional hospitals, provided that:
      (i) said one or more additional hospitals have been provided with literature regarding use of the drug; and
      (ii) said one or more additional hospitals treat said patients and have measures in place to limit use of the drug to short-term use.

54. A method according to claim 53 further comprising the step of:
   (h) dispensing the drug to said patients in said one or more additional hospitals for short-term use.

* * * * *